(12) United States Patent
Christensen

(10) Patent No.: US 7,156,851 B2
(45) Date of Patent: Jan. 2, 2007

(54) IMPLANT AND PROCESS OF MODIFYING AN IMPLANT SURFACE

(75) Inventor: John Christensen, Nordborg (DK)

(73) Assignee: Danfoss A/S, Nordborg (DK)

( * ) Notice: Subject to any disclaimer, the term of this patent is extended or adjusted under 35 U.S.C. 154(b) by 305 days.

(21) Appl. No.: 10/469,012

(22) PCT Filed: Feb. 12, 2002

(86) PCT No.: PCT/DK02/00099

§ 371 (c)(1),
(2), (4) Date: Aug. 26, 2003

(87) PCT Pub. No.: WO02/068007

PCT Pub. Date: Sep. 6, 2002

(65) Prior Publication Data

US 2004/0068323 A1    Apr. 8, 2004

(30) Foreign Application Priority Data

Feb. 26, 2001    (DK) .............................. 2001 00314

(51) Int. Cl.
*A61B 17/86*    (2006.01)
*A61F 2/28*    (2006.01)

(52) U.S. Cl. .............. 606/72; 623/23.53; 427/2.26

(58) Field of Classification Search ............ 623/23.53; 427/531; 148/668
See application file for complete search history.

(56) References Cited

U.S. PATENT DOCUMENTS

| 4,400,408 A | * | 8/1983 | Asano et al. ................. 419/8 |
| 4,743,308 A | | 5/1988 | Sioshansi et al. |
| 5,415,704 A | | 5/1995 | Davidson |
| 6,063,442 A | * | 5/2000 | Cohen et al. ............... 427/250 |

FOREIGN PATENT DOCUMENTS

| DE | 199 40 970 A1 | 1/2001 |
| EP | 0 560 279 A1 | 9/1993 |
| WO | WO 99/26673 | 6/1999 |
| WO | WO 99 65537 | 12/1999 |
| WO | WO 00 38753 | 7/2000 |

* cited by examiner

*Primary Examiner*—David H. Willse
(74) *Attorney, Agent, or Firm*—McCormick, Paulding & Huber LLP

(57) ABSTRACT

An implant and a process of modifying an implant surface, which implant is in particular a hip implant, a tooth implant, a bone screw, fixation pin or a fixation nail (pin-fixation), comprising a metallic base body, which implant has a surface modified by a material containing a tissue-friendly metal, such as tantalum or niobium, for the formation of a surface modification where at least the tissue-friendly metal is alloyed with the surface and constitutes a uniform, diffusion-tight outer zone on the body, which outer zone has a higher ductility than the metallic base body in order to obtain a tissue-friendly implant with increased fatigue strength.

13 Claims, 3 Drawing Sheets

IMPLANT AND PROCESS OF MODIFYING AN IMPLANT SURFACE

CROSS-REFERENCE TO RELATED APPLICATIONS

This application is entitled to the benefit of and incorporates by reference essential subject matter disclosed in International Application No. PCT/DK02/00099 filed on Feb. 12, 2002 and Danish Patent Application No. PA 2001 00314 filed on Feb. 26, 2001.

FIELD OF THE INVENTION

The present invention relates to an implant, in particular a hip implant, a tooth implant, a bone screw, a fixing pin or a fixing nail (pin-fixation), comprising a metallic base body, which base body has a surface being modified by a material with a tissue-friendly metal chosen among tantalum and niobium for the formation of a surface modification.

BACKGROUND OF THE INVENTION

Implants to be inserted in the human organism must or should fulfil several requirements, e.g. that the implant should not release dangerous substances or cause allergic reactions from the patient. Obviously, this applies in particular to the implants intended for permanent or lasting placement in the organism, but neither pin-fixations which are often removed after a few weeks or months should release dangerous substances or cause allergic reactions. Pin-fixations could be pins or nails which are inserted through the tissue to a bone, and these pins or nails are mutually connected to an outer support, the ends of e.g. a broken bone being secured in a correct position and the load being transmitted by the pins and support. Pin-fixations may also be used alone in a bone in order to hold together bone parts when healing and in this case, the pin-fixations will often be left in the body, thus avoiding further operations which may be traumatic and furthermore create more cicatricial tissue.

However, many implants have been produced from materials which do not fulfil this requirement, for example, one material often used is an alloy of cobalt, chrome and molybdenum (CoCrMo) (e.g. Vitallium® containing 60% Co, 35% Cr and 5% Mo). It has appeared that the cobalt content, among others, in CoCrMo is dissolved and diffused out of the implant and into the bloodstreams, which is strongly undesirable since it may result in poisoning and injuries of organs, including the heart. Another material often used for implants is stainless steel alloyed with nickel which is also an undesired substance as it may cause allergy. On the other hand, pure titanium is relatively tissue-friendly and can be used for implants essentially without inconvenience in respect of allergy or poisoning. However, pure titanium is less suitable for implants which are exposed to major mechanical forces, such as hip implants, as implants of pure titanium do not have the same good strength properties as the above-mentioned materials and thus, implants of pure titanium are to a higher degree exposed to fracture than implants of the other materials. Therefore, different titanium alloys have been developed with improved strength properties, but also in this case, the alloy substances may cause allergy or poisoning.

In prior art, several attempts have been made to prevent the implant from releasing poisonous substances or causing allergic reactions. It is thus well described how the implant can be coated with a tissue-friendly material. WO 99/65537 discloses a metallic implant with a surface or a surface coating consisting of several layers of e.g. tantalum in layer thickness of 5 µm or more. This implant has the substantial disadvantage that the coating may peel off as so far it has in practice been impossible to make the layers adhere properly to each other and to the subjacent base body. Of course, the peeling is particularly a problem with implants which are driven into a bone with great force or which are exposed to major loads when inserted in the body. In addition to lacking the desired function as protection against release of unwanted substances from the implant, the peeling of the coating has further the disadvantage that the fixation of the implant is defective in these areas.

In order to avoid peeling of a coating, U.S. Pat. No. 4,743,308 discloses a process of passivation of a metal alloy, especially a Co—Cr—Mo alloy (Vitallium®) with a coating of tissue-friendly material, such as a noble metal, and exposing the coated surface to a bombardment by an ion beam which drives the coating into the metal alloy such that there is no surface layer which can peel off. However, the ion beam bombardment causes that the surface of the implant is not impervious, but almost porous, as it will be spotted with small so-called pin-holes from the ion beam bombardment, and thus, there is a risk that the implant still releases noxious substances.

Furthermore, certain types of implants are exposed to very heavy mechanical loads, e.g. implants for femurs, hip socket and knee, and these implants must therefore fulfil some severe strength conditions. This is becoming more important as in addition to elderly people needing implants because of attrition and fracture, e.g. if they suffer from osteoporosis, there is an increase in the number of young people who need such implants due to acute injuries and attrition resulting from extreme sport activities or the like. It has turned out that knee and hip implants have a durability of 10–15 years which is sufficient in many cases for elderly people, but not for young people. This is due to the fact that it is difficult and often impossible to re-operate, so often an implant cannot be replaced by another as the operation is a major surgical intervention which may be disabling when repeated.

U.S. Pat. No. 5,415,704 discloses a surface hardened, metallic implant where the implant is produced from a metallic alloy added with a dissolved, slightly oxidizable or nitridable metal, such as tantalum. The object is to form an oxidized or nitrided surface layer which can both seal the surface in order to prevent release of poisonous substances and harden the surface in order to obtain a high abrasion resistance of the implant. However, this implant does not have a diffusion-tight, uniform surface and the hardened surface might crack at a bending or fluctuating load as the surface will be relative brittle and cannot follow the movements of the base body.

WO 99/26673 discloses an implant provided with a surface layer. The thickness of the surface layer is chosen such that it is less than the critical defect size for the actual material and stresses. The surface layer may consist of calcium phosphate or an oxide of titanium, zirconium or tantalum. It is indicated that the thickness of the surface layer preferably is less than 5 µm. The object of this invention is to provide a maximal thickness of a surface layer of a material with low strength to prevent the formation of fissures in the layer which may initiate cracks in the base body such that the strength of the implant will be less.

Finally, DE 19940970 discloses a process for an implant of titanium or a titanium alloy with a protection layer of TiO$_2$ and further a surface coating with calcium. However, this patent was published only after the priority date of the present application.

SUMMARY OF THE INVENTION

One object of the present invention is to provide an implant which does not release noxious substances and which has a surface that cannot peel off.

A second object of this invention is to provide an implant with an improved mechanical strength.

The implant according to the invention is characterized in that at least the tissue-friendly metal is alloyed into the surface, said surface modification comprising an alloy zone and a uniform, diffusion-tight outer zone on the base body, which outer zone has a higher ductility than the metallic base body.

The tissue-friendly metal is alloyed into the surface and this means that a metal body in a hardened form is exposed to a process which alloys another metal to the surface of the body, and that the surface thus has an alloy zone, the alloyed metal diffusing up to some micrometers into the body. The application of the alloyed metal continues until it forms an outer zone with a uniform, diffusion-tight surface of essentially pure tissue-friendly metal. The tight outer zone proceeds gradually to the alloy zone which is structurally anchored completely in the base body. The outer zone has a higher ductility than the metallic base body, i.e. that the outer zone has a higher deformation ability than the base body such that the outer zone can be extended longer than the base body.

When producing implants, micro and macro cracks are formed on the surface of the metallic base body, and these cracks cannot be completely removed by subsequent treatment, even by polishing with e.g. diamond paste. Furthermore, the surface of the base body will be provided with grain boundaries, and both grain boundaries and cracks cause notch effect during fatigue, thus facilitating the initiation of crack growth from the surface of the base body, which may lead to fractures. As the outer zone is uniform and impervious, all cracks and grain boundaries on the surface of the base body is efficiently sealed. The implant surface is free from notch effect, the surface being without grain boundaries, cracks or anything from where a crack may initiate, which entails that the fatigue strength is substantially increased. The strength fatigue is of crucial importance to the durability of implants as most implants are exposed to repeated load. A hip implant at ordinary walk will thus be affected about once per second, which means that for a person being out of bed for about 5 hours a day, the total number of loads in a year will be more than 6.5 million. Further, the higher ductility of the outer zone in relation to the base body means that this zone follows the movements of the base body and does not peel off.

An impervious surface without micro porosities is advantageous as bacteria have more difficulties in adhering to an impervious surface, and there is thus less risk of introducing bacteria when inserting the implant. This means that the healing process is not impeded by bacteria and the risk of complications is minimized.

According to a preferred embodiment, the metallic base body is a Co—Cr—Mo alloy which has proved to obtain a particularly high increase of fatigue strength by surface modification.

In a preferred embodiment, the base body is modified by a fused salt process to a thickness of the outer zone of about 2–14 µm, preferably more than 5 µm and less than 12 µm, and in particular 8–10 µm. A thickness of the outer zone of 2 µm may be sufficient by simple geometrical forms of the base body, but with holes and edges, the modification will result in a thinner outer zone and thus a risk of a porous surface. A thickness of the outer zone of more than 14 µm will entail an increase of the process time and more considerable material expenses, and this will thus be unfavourable for economic reasons. It has turned out that a thickness of the outer zone of 8–10 µm makes a reasonable compromise between certainty of a sufficiently thick outer zone over the entire base body and economy.

In an alternative embodiment, the base body is modified by a CVD process to a thickness of the outer zone of about 10–35 µm, preferably more than 12 µm and less than 25 µm, and in particular 12–17 µm. The necessary thickness of the outer zone is larger by this process, as the modification is effected by columnar growth, which entails a risk of pinholes in the surface of thin layers. A thickness of 10 µm will be sufficient by simple forms of the base body, but at holes and edges the outer zone will be thinner, and there will thus be a risk of a porous surface. A thickness of the outer zone of more than 35 µm will entail an increase of the process time and more important material costs, and this will thus be unfavourable for economic reasons. It has turned out that a thickness of the outer zone of 12–17 µm makes a reasonable compromise between guarantee of a sufficiently thick outer zone over the entire base body and economy.

The implant according to the invention may be modified with any suitable material containing a tissue-friendly metal chosen among tantalum or niobium, however, in a preferred embodiment, the tissue-friendly metal is tantalum. It has turned out that this material has particularly good properties, both as to tissue-friendliness, alloying into the base body, improvement of the fatigue strength of the implant, and corrosion resistance.

According to a preferred embodiment, the implant is characterized in that the tissue-friendly metal is α-tantalum. Tantalum can as a number of other metals in a solid state occur in more than one type of crystal lattice. Tantalum may thus occur as α-tantalum with a body-centred cubic lattice and as β-tantalum with a tetragonal lattice. In this connection, α-tantalum is preferable as it is to a much higher extent than β-tantalum dense and ductile.

According to a preferred embodiment, the implant is further characterized in that the implant has compressive stresses in the surface. This contributes to an increase of the fatigue strength of the implant as a possible tensile load will be counteracted by these compressive stresses, and opening of cracks will be counteracted.

The implant is according to an embodiment characterized in that the surface modification also comprises an alloy zone alloyed into the surface of the base body as in the alloy zone there is a gradually increasing concentration of the modification material in the direction the surface of the outer zone, whereas the concentration of the alloy of the base body decreases gradually in the direction of the surface of the outer zone. This alloy zone assures a good adhesive power of the outer zone such that it is to a particularly high degree assured that the outer zone does not peel off or crack.

According to a preferred embodiment, the implant is characterized in that the implant has strength properties essentially corresponding to the strength properties of the bone in which the implant is inserted. This is to be seen in the light of the fact that the modulus of elasticity in bones is about 21,000 MN/m$^2$, whereas e.g. in steel it is about 10 times as large, i.e. about 210,000 MN/m$^2$. The same applies to the tensile strength in bones which is about 140 MN/m², whereas the tensile strength in typical high-tensile steel is up to 1,500 MN/m².

Since the outer zone, as mentioned earlier, has a higher ductility than the base body, the implant can be made with strength properties close to those of the bone, and also yield a little by load without any risk for the outer zone to peel off. In heavy loaded implants, such as hip implants, in order to counteract bone changes, it is particularly advantageous that the implant has strength properties close to the strength properties of the bones in the body. It is thus assured that no stress concentration occurs to increase the risk of fracture or an abnormal growth of the bone, or if the bone implant is much stronger than the bone, the risk that the bone shrinks in the areas where the bone is relieved by the implant.

Furthermore, the surface can be further modified by an ingrowth-promoting substance, such as calcium or hydroxyapatite. Thus, a good adhesion of the implant is assured without using cement or another fixation material.

The implant is in particular a fixation pin or a fixation nail (pin-fixation) with a diameter less than 10 mm. It is an advantage with as small dimensions as possible in connection with pin-fixations as they are to be inserted through the tissue and into the bone and are often removed after some weeks, and the inconveniences in this connection will be less the smaller dimensions by which these pin-fixations can be produced. The small outer dimensions are possible as pin-fixations with surface modification according to the invention have a higher fatigue strength and can thus be produced with smaller dimensions such that the hole in the tissue and bone will be smaller.

The invention further relates to a process of modifying an implant surface which process modifies a surface of an implant, in particular a hip implant, a tooth implant, a bone screw or the like, comprising a metallic base body, which implant is modified by a material containing a tissue-friendly metal chosen among tantalum and niobium.

The process according to the invention is characterized in that the modification comprises a CVD or fused salt process with the tissue-friendly material which is alloyed into the surface of the body by the process, whereby the surface has an alloy zone, the alloyed material diffusing up to some micrometers into the body, and the supply of material continues until an outer zone has been formed with a uniform, diffusion-tight surface of essentially pure tissue-friendly metal, the alloy zone passing gradually into the diffusion-tight outer zone.

BRIEF DESCRIPTION OF THE DRAWINGS

In the following, the invention will explained in more detail by means of embodiments and with reference to the accompanying drawing, in which FIG. 1 schematically shows a sectional view of a surface modified base body.

DETAILED DESCRIPTION OF THE PREFERRED EMBODIMENTS

Figure 1:
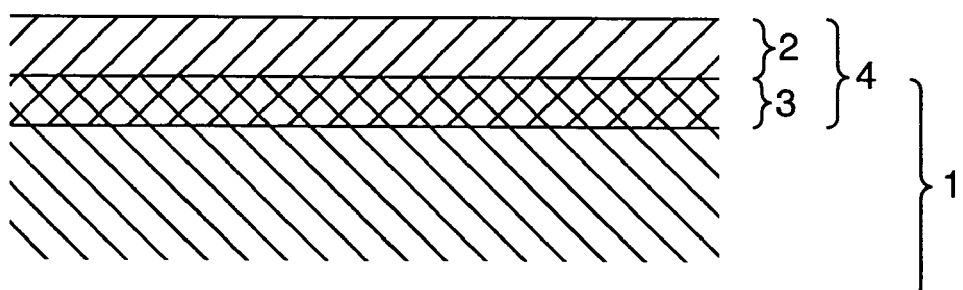

FIG. 1 schematically shows a base body 1 with a surface modification 4 comprising an alloy zone 3 and an outer zone 2, where the modification material in the alloy zone 3 has penetrated the base body 1, whereas the outer zone 2 consists of pure modification material. Because of this structure, the surface modification 4 is securely anchored to the base body 1, thus it is not a coating in a common sense. The thickness of the alloy zone 3 is different depending on the material from which the base body 1 is produced, thus the alloy zone 3 can be in the order of 0.5 μm–1.5 μm for tantalum on Co—Cr—Mo, whereas it is up to 1–10 μmm for tantalum on stainless steel, and 8–10 μm for tantalum on a titanium alloy.

Other types of tissue-friendly metal than tantalum may be used, however, it has turned out that this material has particularly good properties as to tissue-friendliness, alloying into the base body, improvement of the fatigue strength of the implant and resistance to corrosion. Thus, tantalum is more resistant to corrosion than gold, and at room temperature, has a higher resistance to most acids and bases. By way of example, a test body of stainless, surgical steel (316L) with a diffusion-tight outer zone of tantalum exposed to an aggressive hydrochloric acid fog was without a trace of breakdown in the tantalum surface after 30 days, where test bodies without the diffusion tight outer zone corrodes away in a few minutes. In the test, a half-filled container with 40% hydrochloric acid in an aqueous solution was used, at a temperature of 75° C., whereby a gas phase will be formed above the fluid surface—a hydrochloric acid fog which is very aggressive. Test bodies of 6 to 13 mm in diameter were used, and these test bodies were immersed halfway into the fluid, such that the rest was in the gas phase.

The thickness of the outer zone 2 is determined according to the fact that the outer zone 2 has to be uniform and diffusion-tight, and according to an embodiment in which a fused salt process is used, the thickness of the outer zone 2 is 8–10 μm. In another embodiment, a CVD process is used, which requires a thickness of the outer zone 2 of 15–25 μm before it is assured that the outer zone 2 is uniform and diffusion-tight.

In the fused salt process, a base body 1 is lowered in a bath of melted salt to be covered by a material. Not any metal can withstand being lowered in a salt melt as the melt is strongly reactive, and thus e.g. titanium will be dissolved in a moment (fluoride salt melt). At appropriate control by electric impulses, a uniform diffusion-tight outer zone 2 of tantalum can be obtained with a thickness of the outer zone 2 of about 8–10 μm, and a so-called smooth surface is obtained which is completely even and smooth without grain boundaries. An even and smooth surface is advantageous as there is a minimum risk of bacteria on the surface when inserting the implant.

Another possibility is the CVD process (Chemical Vapour Deposition) which is a gas chemical process where a material is vaporized and by means of a carrier gas is brought to a base body where the material is deposited on the surface under columnar growth. Because of the columnar growth, a thickness twice or three times bigger of the outer zone 2 is required before this is uniform and diffusion-tight without pin-holes. On the other hand, the process is environmentally advantageous compared to the fused salt process, and this process also permits to obtain a good surface modification of inner surfaces, holes, etc. However, this process is carried out at temperatures of about 900° C., which may be a problem in connection with e.g. titanium and its alloys as a undesired large grain growth may occur at these temperatures.

On the other hand, it is not possible to use e.g. the PVD process (Physical Vapour Deposition), as this process gives an entirely porous surface with a large number of pin-holes per square centimeter. Furthermore, no outer zones at all can be provided with the necessary thickness, as the material will deposit as a layer on the surface of the base body without actual alloying, the PVD process taking place at temperatures below 300° C., and therefore the layer will tend to peel off at a thickness of more than 2–3 µm.

Figure 2:
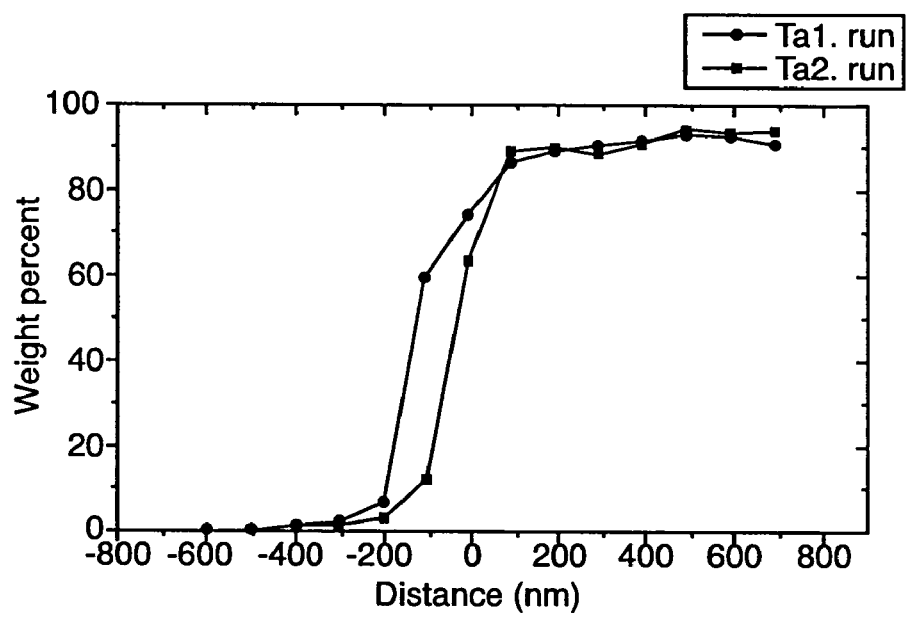
FIG. 2 shows a graph indicating the quantity of tantalum which has penetrated a base body of a Co—Cr—Mo alloy.

By the CVD and fused salt process, an alloy of the modification material is obtained in the surface of the base body 1, the modification material diffusing a little into the base body 1. This is seen from, among others, FIG. 2 showing a measurement of the content of tantalum at different distances from the surface of a base body produced from Co—Cr—Mo and surface modified by tantalum. In FIG. 2, a distance of zero represents the surface of the base body 1, negative values positions in the base body 1 and the alloy zone 3, whereas positive values represent positions in the outer zone 2. It can thus be seen that in a depth of 100 nm (0.1 µm), there is a weight percentage about 40 of tantalum. This indicates that even in a base body made from Co—Cr—Mo having a rather closed surface, an alloy of tantalum takes place in the base body 1 which assures a complete anchoring of the outer zone 2, and thus that the outer zone 2 does not peel off.

Figure 3:
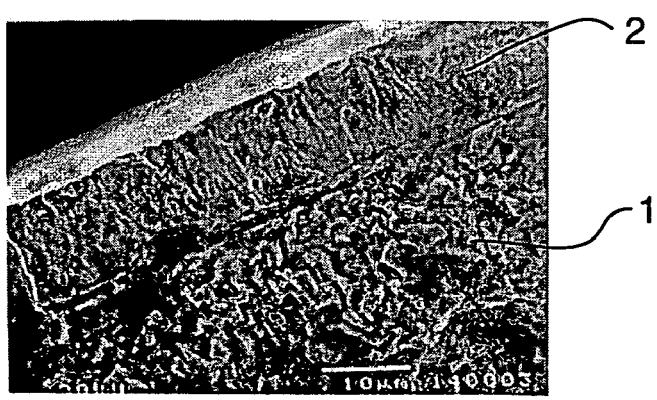
FIG. 3 shows an enlargement at 600 magnification in an electron microscope of a base body with surface modification.

FIG. 3 shows a sectional view of a surface modified base body 1 produced from a Co—Cr—Mo alloy modified by tantalum by a fused salt process. The outer zone 2 on the base body 1 has in this embodiment a thickness of about 15 µm. It has turned out that the thickness of the outer zone 2 when modified by tantalum by the fused salt process does not need to be larger than about 10 µm, however, there is nothing to prevent much thicker outer zones 2, e.g. of 50 µm.

Figure 4:
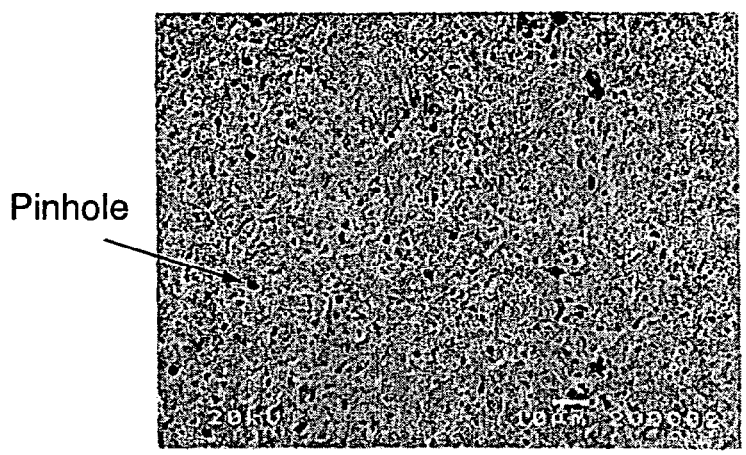
FIG. 4 is a surface modified surface with pin-holes.
Figure 5:
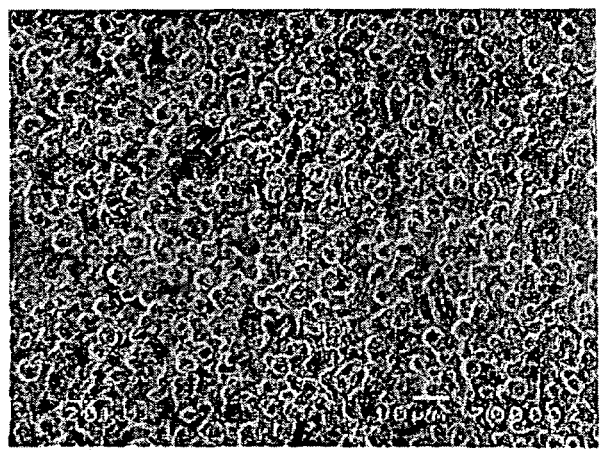
FIG. 5 is a surface modified surface without pin-holes.

As mentioned, it is essential that the outer zone 2 is uniform and diffusion-tight which may be difficult to obtain, especially by the CVD process where the outer zone 2 is built up by columnar growth as there is a risk that pin-holes will appear in the surface, this means that the outer zone 2 is provided with through-going holes. This is seen in FIG. 4 showing the surface of a surface modified base body. The black spots are such pin-holes. FIG. 5 shows a surface of a corresponding surface modified base body, and it can be seen that this surface is impervious and without pin-holes.

Since the implant according to the invention has a uniform and diffusion-tight outer zone, a diffusion barrier is thus provided to assure that unwanted substances in the base body, such as cobalt, do not diffuse out of the implant. As can be seen from FIG. 6 indicating the measured quantity of cobalt in the base body, alloy zone and outer zone of a tantalum modified base body made from a Co—Cr—Mo alloy, the measured quantity of cobalt reduces in the alloy zone 3 from approx. 65% in the base body 1. Again a distance of zero represents the surface of the base body 1, negative values positions in the base body 1 and the alloy zone 3, whereas positive values represent positions in the outer zone 2. In this connection it should be remarked that the figure due to measuring technical limitations provides a somewhat misleading picture. In fact, cobalt is only present in the alloy zone where the quantity gradually approaches zero, whereas no cobalt is found in the outer zone.

Figure 7:
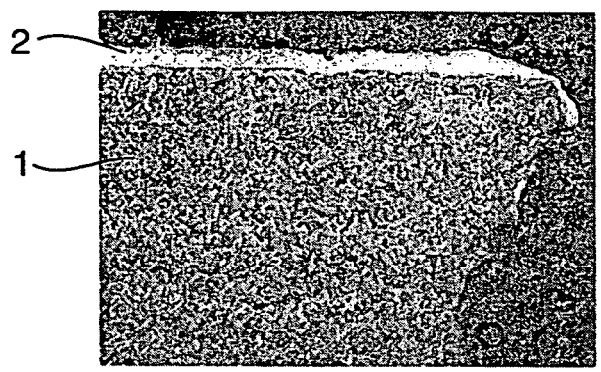
FIG. 7 shows a thin section perpendicular to a fracture zone of a surface modified base body.

FIG. 7 shows a thin section perpendicular to a fracture on a corresponding test piece. It is seen that the outer zone 2 did not loosen or peel off, however, it seems that the outer zone 2 of pure tantalum has yielded just at the fracture, which confirms that the outer zone 2 does not peel off and that the outer zone 2 has a higher ductility than the base body 1.

Figure 8:
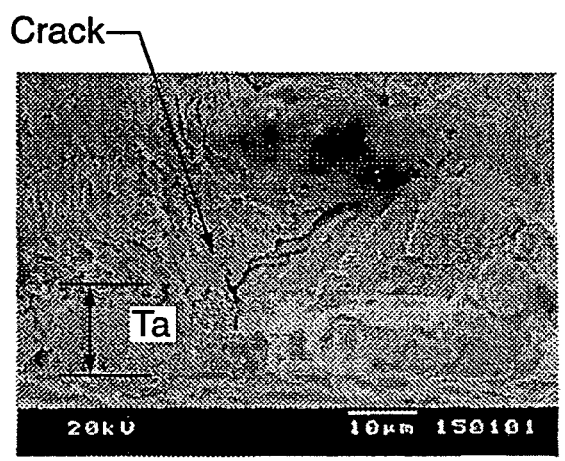
FIG. 8 is a view showing a crack in a base body.

FIG. 8 showing an enlargement of a base body 1 of stainless steel which has been surface modified by tantalum, is an example of a crack which seems to stop in the outer zone 2 of tantalum, which may be due to the fact that the outer zone 2 has a higher ductility than the base body 1, the concentration of stress at a crack tip being reduced, and that there are compressive stresses in the surface of the implant.

The fact is that X-ray analysis has proved that for a base body made from stainless steel and surface modified by tantalum by the fused salt process, there are compressive stresses in the surface of the outer zone of about 300 Mpa. These compressive stresses will contribute to cracks not being formed so easily in the surface, the surface being prestressed and preventing the cracks from opening, as this compressive stress has to be overcome beforehand.

Figure 6:
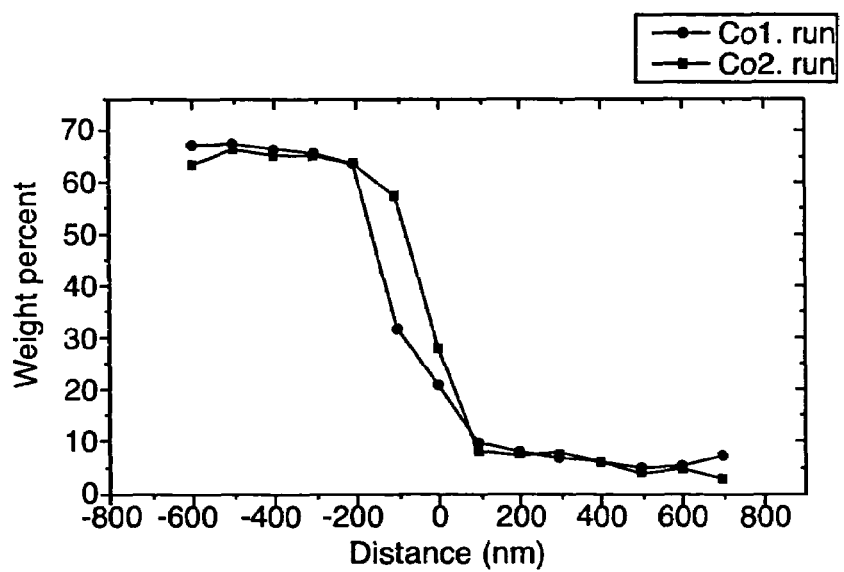
FIG. 6 shows a graph indicating the quantity of Co in the surface area of a tantalum modified base body produced from a Co—Cr—Mo alloy.
Figure 9:
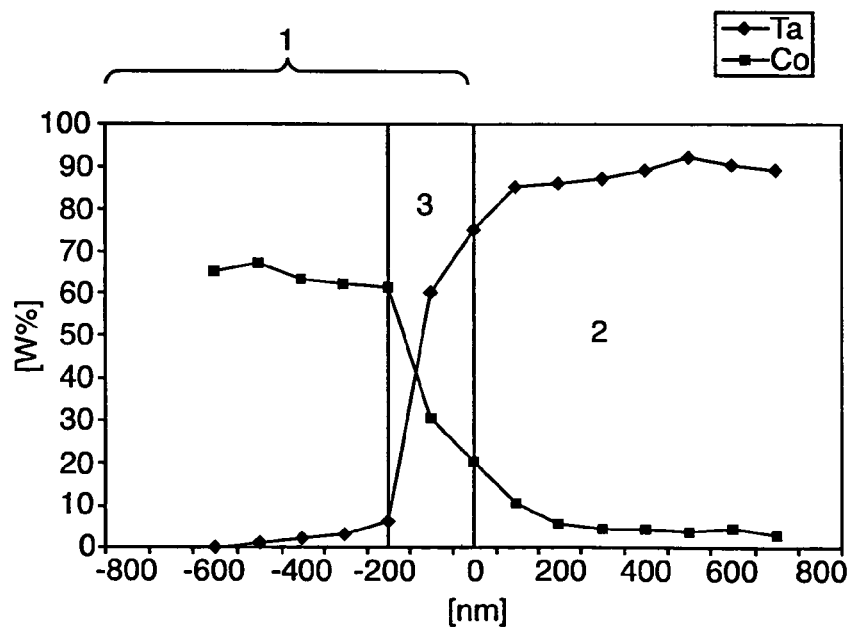
FIG. 9 is a graph with curves for the content of tantalum and cobalt in the area around the surface of the base body.

FIG. 9 is a graph with curves for the content of tantalum and cobalt in the area around the surface of the base body, such that the figure corresponds to a connection of FIGS. 2 and 6. The figure illustrates that in the alloy zone 3, there is a gradually increasing concentration of modification material in the direction of the outer zone 2, whereas the concentration of the alloy of the base body gradually decreases in the direction of the outer zone 2. The outer zone 2 consists almost solely of modification material.

By measurement of the fatigue strength, it has been ascertained that by the invention, there is provided an implant which has improved fatigue strength. A base body produced from stainless steel obtains thus an improvement of the fatigue strength of 20% by a surface modification by tantalum, whereas a base body produced by a Co—Cr—Mo alloy obtains an improvement of the fatigue strength of 60%.

As earlier mentioned, niobium can also be used for the surface modification. When niobium is alloyed in the surface, it must, however, be assured that no oxides are formed as this reduces the adherence considerably.

The invention may also be used for skin lead-throughs and catheters, i.e. the type of implants which are not anchored in a bone. Such lead-throughs are used by ostomy and dialysis for transportation of liquids and substances out of and into the body, but may also be used for electric lines, e.g. in the case where a pacemaker is positioned outside the body. In some cases, the lead-through is of permanent character, and in other cases of temporary character. The lead-through consists of an L, T or I-shaped metal tube, where the surface of the tube is modified according to the invention.

The invention claimed is:

1. An implant comprising:
   a metallic base body having a surface; and
   a material modifying the surface of the base body, the material having a tissue-friendly metal chosen among tantalum and niobium for the formation of a surface modification;
   wherein at least the tissue-friendly metal is alloyed into the surface, the surface modification comprising an alloy zone and a uniform, diffusion-tight outer zone on the base body, which outer zone has a higher ductility than the metallic base body, and wherein the base body is modified by either a fused salt process to a thickness of the outer zone of about 2–14 μm, or a CVD process to a thickness of the outer zone of about 10–35 μm.

2. The implant according to claim 1, wherein the metallic base body is a Co—Cr—Mo alloy.

3. The implant according to claim 1, wherein the base body is modified by a fused salt process to a thickness of the outer zone of about 2–14 μm.

4. The implant of claim 3, wherein the thickness of the outer zone is more than 5 m and less than 12 μm.

5. The implant of claim 3, wherein the thickness of the outer zone is 8–10 μm.

6. The implant according to claim 1 wherein the base body is modified by a CVD process to a thickness of the outer zone of about 10–35 μm.

7. The implant of claim 6, wherein the thickness of the outer zone is more than 12 μm and less than 25 μm.

8. The implant of claim 6, wherein the thickness of the outer zone is 12–17 μm.

9. The implant according to claim 1, wherein the implant is formed with compressive stresses in the surface.

10. The implant according to claim 1, wherein the alloy zone there is a gradually increasing concentration of the modification material in the direction of the surface of the outer zone, whereas the concentration of the alloy of the base body decreases gradually in the direction of the surface of the outer zone.

11. The implant according to claim 1, wherein the implant has strength properties essentially corresponding to the strength properties of the bone in which the implant is to be inserted.

12. The implant according to claim 1, wherein the implant is a fixation pin or a fixation nail (pin-fixation) with a diameter less than 10 mm.

13. The implant according to claim 1, wherein the surface of the implant is further modified by an ingrowth-promoting substance.

* * * * *